United States Patent
Chen et al.

(10) Patent No.: US 11,572,365 B2
(45) Date of Patent: Feb. 7, 2023

(54) CRYSTAL FORM OF UPADACITINIB, PREPARATION METHOD THEREFOR, AND USE THEREOF

(71) Applicant: CRYSTAL PHARMACEUTICAL (SUZHOU) CO., LTD., Jiangsu (CN)

(72) Inventors: Minhua Chen, Jiangsu (CN); Jing Zhang, Jiangsu (CN)

(73) Assignee: CRYSTAL PHARMACEUTICAL (SUZHOU) CO., LTD., Suzhou (CN)

( * ) Notice: Subject to any disclaimer, the term of this patent is extended or adjusted under 35 U.S.C. 154(b) by 0 days.

(21) Appl. No.: 17/700,273

(22) Filed: Mar. 21, 2022

(65) Prior Publication Data

US 2022/0204519 A1    Jun. 30, 2022

Related U.S. Application Data

(63) Continuation of application No. PCT/CN2021/101784, filed on Jun. 23, 2021.

(51) Int. Cl.
*C07D 487/14* (2006.01)

(52) U.S. Cl.
CPC ........ *C07D 487/14* (2013.01); *C07B 2200/13* (2013.01)

(58) Field of Classification Search
CPC .................................................. C07D 487/14
See application file for complete search history.

(56) References Cited

FOREIGN PATENT DOCUMENTS

| | | | |
|---|---|---|---|
| GN | 108368121 A | 8/2018 | |
| WO | 2009152133 A1 | 12/2009 | |
| WO | 2011068881 A1 | 6/2011 | |
| WO | 2015061665 A1 | 4/2015 | |
| WO | 2017066775 A1 | 4/2017 | |
| WO | WO-2017066775 A1 * | 4/2017 | ......... A61K 31/4985 |
| WO | 2018165581 A1 | 9/2018 | |
| WO | 2020063939 A1 | 4/2020 | |
| WO | 2020115212 A1 | 6/2020 | |
| WO | 2020115213 A1 | 6/2020 | |
| WO | 2020177645 A1 | 9/2020 | |
| WO | 2021067465 A1 | 4/2021 | |
| WO | 2021244323 A1 | 12/2021 | |

OTHER PUBLICATIONS

International Application No. PCT/CN2021/101784, International Search Report and Written Opinion dated Sep. 26, 2021, 14 pages.

* cited by examiner

*Primary Examiner* — Samira J Jean-Louis
(74) *Attorney, Agent, or Firm* — MagStone Law, LLP; Enshan Hong

(57) ABSTRACT

Crystalline forms of upadacitinib and processes for preparation thereof are disclosed. The present disclosure also relates to pharmaceutical compositions containing the upadacitinib crystalline forms, use of the upadacitinib crystalline forms for preparing JAK1 inhibitor drugs, and use of the upadacitinib crystalline forms for preparing drugs treating rheumatoid arthritis, Crohn's disease, ulcerative colitis, atopic dermatitis and psoriatic arthritis. The crystalline forms of upadacitinib provided by the present disclosure have one or more improved properties compared with prior arts and have significant values for future drug optimization and development.

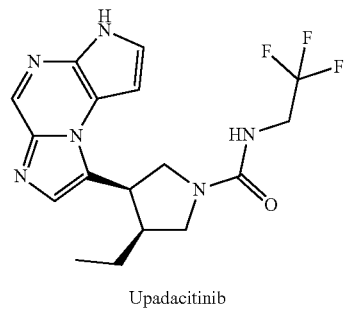

Upadacitinib

16 Claims, 9 Drawing Sheets

CRYSTAL FORM OF UPADACITINIB, PREPARATION METHOD THEREFOR, AND USE THEREOF

RELATED APPLICATIONS

This is a continuation application of PCT/CN2021/101784 filed on Jun. 23, 2021, which claims priority to China Patent Application Nos. 202010991590.4 and 202010653055.8 respectively filed on Sep. 17, 2020, and Jul. 8, 2020, with China National Intellectual Property Administration (CNIPA), all of which are incorporated herein by reference in their entirety.

BACKGROUND OF THE INVENTION

1. Technical Field

The present disclosure relates to the field of chemical crystallography, particularly relates to novel crystalline forms of upadacitinib, processes for preparation and uses thereof.

2. Background Art

Rheumatoid arthritis is an autoimmune disease that can cause chronic inflammation in joints and other parts of the body and leads to permanent joint damage and deformities. If not treated, rheumatoid arthritis can lead to substantial disability and pain due to the damage of joint function, which ultimately leads to shorter life expectancy. Crohn's disease is an inflammatory bowel disease. Symptoms usually include abdominal pain, diarrhea, fever, and weight loss. Those with this disease are at higher risk of colon cancer. Ulcerative colitis is a chronic disease that causes inflammation and ulcers of colon and rectum. The main symptoms are abdominal pain and diarrhea with bloody stools. The symptoms usually progress slowly and vary in severity. The common symptoms of atopic dermatitis include itchy, redness, and cracked skin. Patients with atopic dermatitis may also have hay fever and asthma. Psoriatic arthritis is an inflammatory arthropathy associated with psoriasis, with a psoriasis rash and accompanied with pain, swelling, tenderness and stiffness in the joints and surrounding soft tissues, and dyskinesia.

Janus kinase 1 (JAK1) is a target for immune-inflammatory diseases, and its inhibitors are beneficial for the treatment of immune-inflammatory disorders diseases, such as rheumatoid arthritis, Crohn's disease, ulcerative colitis, atopic dermatitis, psoriatic arthritis, etc. Upadacitinib is a second-generation oral JAK1 inhibitor developed by AbbVie, with a high inhibition selectivity for JAK1. The chemical name of upadacitinib is: (3S,4R)-3-ethyl-4-(3H-imidazo[1,2-a] pyrrolo[2,3-e] pyrazin-8-yl)-N-(2,2,2-trifluoroethyl) pyrrolidine-1-carboxamide, and the structure is shown as follows:

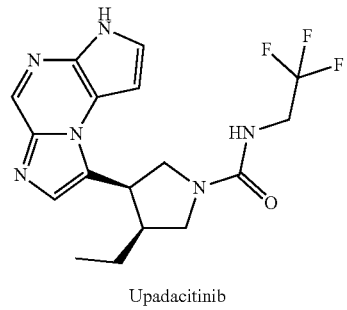 [SMILES: CC[C@@H]1CN(C(=O)NCC(F)(F)F)C[C@@H]1c1cnc2cnc3[nH]ccc3n12]

Upadacitinib

A crystalline form is a solid material whose constituents are arranged in a highly ordered microscopic structure, forming a crystal lattice that extends in all directions. Compounds may exist in one or more salts, crystalline forms, or co-crystals, but their existence and characteristics cannot be predicted with any certainty. Different crystalline forms of drug substances have different physicochemical properties, which can affect drug's in vivo dissolution and absorption and will further affect drug's clinical efficacy and safety to some extent. In particular, for some poorly soluble oral solid or semi-solid dosage forms, crystalline forms can be crucial to the performance of drug product. In addition, the physical properties of a crystalline form may be important to the manufacturing process. For example, a certain polymorph might be prone to solvate formation or has poor impurity rejection capabilities. Therefore, polymorphism is an important part of drug research and drug quality control.

Amorphous forms are non-crystalline materials which possess no long-range order. Typically, an amorphous form will exhibit a broad "halo" XRPD pattern. The molecules in the amorphous solids are randomly arranged. Because of the poor thermodynamic stability of an amorphous drug substance, it is prone to crystal transformation during the manufacturing process and storage. The poorly stable amorphous drug substance may lead to the change of drug bioavailability, dissolution rate, etc., resulting in changes in the drug's clinical efficacy.

According to "FDA Regulatory Classification of Pharmaceutical Co-Crystals Guidance for Industry", pharmaceutical co-crystals are crystalline materials composed of two or more different molecules (one of which is the API) in the same crystal lattice that are associated by nonionic and noncovalent bonds. One advantage of pharmaceutical co-crystals is to enhance drug product bioavailability and stability. Another advantage of co-crystals is that they generate better solid-state forms for APIs that lack ionizable functional groups, which is a prerequisite for salt formation. Succinic acid and adipic acid are both listed in Generally Recognized as Safe (GRAS) and FDA Inactive Ingredient Database, indicating succinic acid and adipic acid are safe pharmaceutical co-crystal formers.

WO2017066775A1 disclosed upadacitinib free form Form A, Form B, Form C, Form D, amorphous and salts thereof. This patent application disclosed that Form A and Form B have poor crystallinity and stability, and can be easily dehydrated to amorphous. Form D can only be obtained at low water activity. In addition, the crystallization process of Form D is slow and difficult to repeat. Form D will convert to Form C at high water activity. Compared with other forms of upadacitinib free form disclosed in WO2017066775A1, Form C has better properties. However, it has disadvantages of poor repeatability and is difficult to crystallize from solution.

WO2020063939A1 disclosed an acetic acid solvate of upadacitinib (Form CSI). WO2020115213A1 disclosed acetic acid solvate forms $A_{HOAC}/B_{HOAC}$, wherein form $A_{HOAC}$ is the same as form CSI. The inventors of the present disclosure found that the stability of the acetic acid solvates is poor and the acetic acid solvates do not meet the requirements of pharmaceutical development.

In order to overcome the disadvantages of prior arts, a crystalline form meeting the pharmaceutical requirements is still needed for the development of drugs containing upadacitinib. The inventors of the present disclosure surprisingly discovered crystalline form CSVI and crystalline form CSVII of upadacitinib, which have advantages in at least one aspect of solubility, hygroscopicity, purification ability, stability, adhesiveness, compressibility, flowability, in vitro and in vivo dissolution, and bioavailability, etc. In particular, crystalline form CSVI and crystalline form CSVII have good solubility, good stability, high dissolution, and safe co-crystal formers, which solves the problems existing in the prior art and is of great significance for the development of drugs containing upadacitinib.

SUMMARY OF THE INVENTION

The present disclosure is to provide novel crystalline forms of upadacitinib, processes for preparation, pharmaceutical compositions and use thereof.

According to the objective of the present disclosure, succinic acid co-crystal form CSVI of upadacitinib is provided (hereinafter referred to as Form CSVI).

According to one aspect of the present disclosure, the X-ray powder diffraction pattern of Form CSVI shows one or two or three characteristic peaks at 2theta values of 4.7°±0.2°, 6.2°±0.2° and 22.7°±0.2° using CuKα radiation. Preferably, the X-ray powder diffraction pattern of Form CSVI shows characteristic peaks at 2theta values of 4.7°±0.2°, 6.2°±0.2° and 22.7°±0.2° using CuKα radiation.

Furthermore, the X-ray powder diffraction pattern of Form CSVI shows one or two or three characteristic peaks at 2theta values of 15.8°±0.2°, 17.3°±0.2° and 23.5°±0.2° using CuKα radiation.

Preferably, the X-ray powder diffraction pattern of Form CSVI shows characteristic peaks at 2theta values of 15.8°±0.2°, 17.3°±0.2° and 23.5°±0.2° using CuKα radiation.

Furthermore, the X-ray powder diffraction pattern of Form CSVI shows one or two or three characteristic peaks at 2theta values of 11.1°±0.2°, 14.1°±0.2° and 13.1°±0.2° using CuKα radiation.

Preferably, the X-ray powder diffraction pattern of Form CSVI shows characteristic peaks at 2theta values of 11.1°±0.2°, 14.1°±0.2° and 13.1°±0.2° using CuKα radiation.

According to another aspect of the present disclosure, the X-ray powder diffraction pattern of Form CSVI shows three or four or five or six or seven or eight or nine or ten or eleven or twelve characteristic peaks at 2theta values of 4.7°±0.2°, 6.2°±0.2°, 22.7°±0.2°, 15.8°±0.2°, 17.3°±0.2°, 23.5°±0.2°, 11.1°±0.2°, 14.1°±0.2°, 13.1°±0.2°, 20.2°±0.2°, 16.2°±0.2° and 21.3°±0.2° using CuKα radiation. Preferably, the X-ray powder diffraction pattern of Form CSVI shows characteristic peaks at 2theta values of 4.7°±0.2°, 6.2°±0.2°, 22.7°±0.2°, 15.8°±0.2° and 14.1°±0.2° using CuKα radiation.

Without any limitation being implied, the X-ray powder diffraction pattern of Form CSVI is substantially as depicted in FIG. 1.

Without any limitation being implied, the Thermo Gravimetric Analysis (TGA) curve of Form CSVI is substantially as depicted in FIG. 2, which shows 1.2% weight loss when heated to 100° C.

Without any limitation being implied, the Differential Scanning Calorimetry (DSC) curve of Form CSVI is substantially as depicted in FIG. 3, which shows an endothermic peak when heated to around 124° C.

Without any limitation being implied, the molar ratio of succinic acid and upadacitinib in Form CSVI is 0.4:1-1.1:1, preferably 0.5:1-1:1.

According to the objective of the present disclosure, a process for preparing Form CSVI is also provided. The process comprises: 1) adding upadacitinib and succinic acid into a mixture of an ester and an ether, stirring to obtain Form CSVI, or 2) adding upadacitinib and succinic acid into a mixture of an ether, an alcohol, water and an alkane or a mixture of an alcohol and an alkane, stirring to obtain Form CSVI.

Furthermore, said ester is preferably isopropyl acetate, said ether is methyl tert-butyl ether, said alcohol is n-propanol, isopropanol, isobutanol or n-butanol, said alkane is n-heptane.

Furthermore, in method 1), upadacitinib and adipic acid were added in a molar ratio of 1:1-1:3. The volume ratio of said ester/ether is 1:1-1:3. Said stirring temperature is preferably 0° C.-50° C. The time of said stirring is preferably more than 12 hours.

Furthermore, in method 2), upadacitinib and adipic acid were added in a molar ratio of 1:0.6-1:2.

Form CSVI of the present disclosure has the following advantages:

(1) Compared with prior arts, Form CSVI has higher solubility. Particularly in FaSSIF, FeSSIF and pH=7.4 PBS, the solubility of Form CSVI is 4-8 times that of Form C of prior art. Higher solubility is beneficial to improve drug's in vivo absorption and bioavailability, thus improving drug efficacy. In addition, drug dose reduction without affecting efficacy is possible due to higher solubility, thereby reducing the drug's side effects and improving drug safety.

(2) Form CSVI drug substance of the present disclosure has good stability. Crystalline state of form CSVI drug substance doesn't change for at least six months when stored under the condition of 40° C./75% RH (relative humidity). Crystalline state of Form CSVI drug substance doesn't change for at least one month when stored under the condition of 60° C./75% RH. The chemical purity is above 99.8% and remains substantially unchanged during storage. After Form CSVI is mixed with the excipients to form a drug product and stored under the condition of 25° C./60% RH and 40° C./75% RH, crystalline state of Form CSVI drug product doesn't change for at least three months. The chemical purity of the drug substance in drug product is above 99.8% and remains substantially unchanged during storage.

Good stability of drug substances and drug products under accelerated and stress conditions is of great importance to the drug development. Drug substance will go through high temperature and high humidity conditions caused by different seasons, regional climate and weather during storage, transportation, and manufacturing processes. Form CSVI drug substance and drug product have good stability under these stress conditions, which are beneficial to avoid the impact on drug quality due to crystal transformation or decrease in purity during drug storage.

Good physical and chemical stability of drug substances ensure that during production and storage, no crystal transformation occurs, and no impurity is generated. Form CSVI has good physical and chemical stability, ensuring consistent and controllable quality of the drug substance and drug product, minimizing quality changes, bioavailability changes, toxicity and side effects caused by crystal transformation or impurity generation.

(3) Compared with prior art, Form CSVI drug product has better in vitro dissolution. In 0.1 N HCl, the dissolution of Form CSVI drug product at 30 minutes is up to 85%, meeting the standards of rapid dissolution. In 0.1 N HCl, the dissolution rate of Form CSVI drug product is higher than that of Form C. It is speculated that Form CSVI has the advantage over Form C in in-vivo bioavailability.

Drug dissolution is a prerequisite to drug absorption. Drugs of different crystalline forms may cause different in vivo dissolution dynamics, which ultimately leads to different clinical efficacy. According to "BCS (Biopharmaceutics Classification System) guidelines", in vitro dissolution testing is a useful tool to forecast the in vivo performance of drug products. Good in vitro dissolution of Form CSVI drug products provided by the present disclosure may leads to higher in vivo absorption, better in vivo exposure, thereby improving drug's bioavailability and efficacy. Higher intrinsic dissolution rate of Form CSVI drug substance is beneficial for the drug to achieve peak concentration in plasma quickly after administration, thus ensuring rapid drug action. According to the objective of the present disclosure, adipic acid co-crystal form CSVII of upadacitinib is provided (hereinafter referred to as Form CSVII).

According to one aspect of the present disclosure, the X-ray powder diffraction pattern of Form CSVII shows one or two or three characteristic peaks at 2theta values of 4.8°±0.2°, 6.0°±0.2° and 22.4°±0.2° using CuKα radiation. Preferably, the X-ray powder diffraction pattern of Form CSVII shows characteristic peaks at 2theta values of 4.8°±0.2°, 6.0°±0.2° and 22.4°±0.2° using CuKα radiation.

Furthermore, the X-ray powder diffraction pattern of Form CSVII shows one or two or three characteristic peaks at 2theta values of 21.1°±0.2°, 15.4°±0.2° and 16.2°±0.2° using CuKα radiation. Preferably, the X-ray powder diffraction pattern of Form CSVII shows characteristic peaks at 2theta values of 21.10°±0.2°, 15.4°±0.2° and 16.2°±0.2° using CuKα radiation.

Furthermore, the X-ray powder diffraction pattern of Form CSVII shows one or two or three characteristic peaks at 2theta values of 25.4°±0.2°, 12.8° 0.2° and 20.2°±0.2° using CuKα radiation. Preferably, the X-ray powder diffraction pattern of Form CSVII shows characteristic peaks at 2theta values of 25.4°±0.2°, 12.8°±0.2° and 20.2°±0.2° using CuKα radiation.

According to another aspect of the present disclosure, the X-ray powder diffraction pattern of Form CSVII shows three or four or five or six or seven or eight or nine or ten or eleven characteristic peaks at 2theta values of 4.8°±0.2°, 6.0°±0.2°, 22.4°±0.2°, 21.1°±0.2°, 15.4°±0.2°, 16.2°±0.2°, 25.4°±0.2°, 12.8°±0.2°, 20.2°±0.2°, 17.4°±0.2° and 21.7°±0.2° using CuKα radiation. Without any limitation being implied, the X-ray powder diffraction pattern of Form CSVII is substantially as depicted in FIG. 6.

Without any limitation being implied, the TGA curve of Form CSVII is substantially as depicted in FIG. 8, which shows 0.1% weight loss when heated to 100° C. Without any limitation being implied, the DSC curve of Form CSVII is substantially as depicted in FIG. 9, which shows an endothermic peak when heated to around 105° C. Without any limitation being implied, the molar ratio of adipic acid and upadacitinib in Form CSVII is 0.4:1-1.1:1, preferably 0.5:1-1:1.

According to the objective of the present disclosure, a process for preparing Form CSVII is also provided. The process comprises: 1) adding upadacitinib and adipic acid into a mixture of an ester and an ether, stirring to obtain Form CSVII, or 2) adding upadacitinib and adipic acid into a mixture of an alcohol and an alkane, stirring, isolating, and then drying to obtain Form CSVII.

Furthermore, said ester is isopropyl acetate, said ether is methyl tert-butyl ether, said alcohol is n-propanol, isopropanol, n-butanol or isobutanol, said alkane is n-heptane. Furthermore, in method 1), upadacitinib and adipic acid were added in a molar ratio of 1:1-1:3. The volume ratio of said ester/ether is 1:1-1:10. Said stirring temperature is preferably 0° C.-50° C. The time of said stirring is preferably more than 12 hours.

Furthermore, in method 2), upadacitinib and adipic acid were added in a molar ratio of 1:0.6-1:2. The temperature of said vacuum drying is preferably 40° C.-80° C.

Form CSVII of the present disclosure has the following advantages:

(1) Compared with prior art, Form CSVII has higher solubility. Particularly in FaSSIF, FeSSIF and pH=7.4 PBS, the solubility of Form CSVII is 4-8 times that of Form C of prior art. Higher solubility is beneficial to improve drug's in vivo absorption and bioavailability, thus improving drug efficacy. In addition, drug dose reduction without affecting efficacy is possible due to higher solubility, thereby reducing the drug's side effects and improving drug safety.

(2) Form CSVII drug substance of the present disclosure has good stability. Crystalline state of Form CSVII drug substance doesn't change for at least six months when stored under the condition of 25° C./60% RH. Crystalline state of Form CSVII drug substance doesn't change for at least six months when stored under the condition of 40° C./75% RH (sealed). Form CSVII drug substance doesn't change for at least one month when stored under the condition of 60° C./75% RH (sealed). The chemical purity is above 99.9% and remains substantially unchanged during storage. After Form CSVII is mixed with the excipients to form a drug product and stored under the condition of 25° C./60% RH and 40° C./75% RH, crystalline state of Form CSVII drug product doesn't change for at least three months. The chemical purity of the drug substance in drug product remains substantially unchanged during storage.

Good stability of drug substances and drug products under accelerated and stress conditions is of great importance to the drug development. Drug substance will go through high temperature and high humidity conditions caused by seasons, regional climate and weather during storage, transportation, and manufacturing processes. Form CSVII has good stability under these stress conditions, which is beneficial to avoid the impact on drug quality due to crystal transformation or decrease in purity during drug storage.

Good physical and chemical stability of drug substances ensure that during production and storage, no crystal transformation occurs, and no impurity is generated. Form CSVII has good physical and chemical stability, ensuring consistent and controllable quality of the drug substance and drug product, minimizing quality changes, bioavailability changes, toxicity and side effects caused by crystal transformation or impurity generation.

(3) Compared with prior art, Form CSVII has better in vitro dissolution. In 0.1 N HCl, the dissolution of Form CSVII drug product at 30 minutes is up to 85%, meeting the standards of rapid dissolution. In 0.1 N HCl and pH6.8 PBS, the dissolution rate of Form CSVII drug product is higher than that of Form C. It is speculated that Form CSVII has the advantage of bioavailability in vivo compared with Form C.

Drug dissolution is a prerequisite to drug absorption. Drugs of different crystalline forms may lead to different in vivo dissolution dynamics, which ultimately leads to different clinical efficacy. According to "BCS (Biopharmaceutics Classification System) guidelines", in vitro dissolution testing is a useful tool to forecast the in vivo performance of drug products. Good in vitro dissolution of Form CSVII drug products provided by the present disclosure may leads to higher in vivo absorption, and better in vivo exposure, thereby improving drug's bioavailability and efficacy. Higher intrinsic dissolution rate of Form CSVII drug substance is beneficial for the drug to achieve peak concentration in plasma quickly after administration, thus ensuring rapid drug action.

According to the objective of the present disclosure, a pharmaceutical composition is provided, said pharmaceutical composition comprises a therapeutically effective amount of Form CSVI or Form CSVII and pharmaceutically acceptable excipients.

Furthermore, the present disclosure also provides the use of Form CSVI or Form CSVII for preparing JAK1 inhibitor drugs.

Furthermore, the present disclosure also provides the use of Form CSVI or Form CSVII for preparing drugs treating rheumatoid arthritis, Crohn's disease, ulcerative colitis, atopic dermatitis and psoriatic arthritis.

In the present disclosure, said "room temperature" is not a specific temperature, but a temperature range of 10–30° C.

In the present disclosure, said "stirring" is accomplished by using a conventional method in the field such as magnetic stirring or mechanical stirring and the stirring speed is 50 to 1800 r/min, preferably the magnetic stirring speed is 300 to 900 r/min and mechanical stirring speed is 100 to 300 r/min.

Said "drying" is accomplished at room temperature or a higher temperature. The drying temperature is from room temperature to about 80° C., or to 60° C., or to 50° C., or to 40° C. The drying time can be 2 to 48 hours, or overnight. Drying is accomplished in a fume hood, forced air convection oven or vacuum oven.

Said "characteristic peak" refers to a representative diffraction peak used to distinguish crystals, which usually can have a deviation of 0.2° using CuKα radiation.

The "solvent saturated with water" is prepared by conventional methods in the art. For example, excess water is ultrasonically mixed with the corresponding solvent, and the organic solvent phase is taken after standing and phase separation.

In the present disclosure, "crystal" or "crystalline form" refers to the crystal or the crystalline form being identified by the X-ray diffraction pattern shown herein. Those skilled in the art are able to understand that the X-ray diffraction pattern errors depend on the instrument conditions, the sample preparation and the purity of samples. The relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. Thus, it will be understood by those skilled in the art that a crystalline form of the present disclosure is not necessarily to have exactly the same X-ray diffraction pattern of the example shown herein. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, Form CSVI and Form CSVII of the present disclosure is pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and furthermore specifically less than 1% (w/w).

In the present disclosure, the term "about" when referring to a measurable value such as weight, time, temperature, and the like, is meant to encompass variations of ±10%, ±5%, ±1%, ±0.5%, or even ±0.1% of the specified amount.

DESCRIPTION OF PREFERRED EMBODIMENTS

Figure 1:
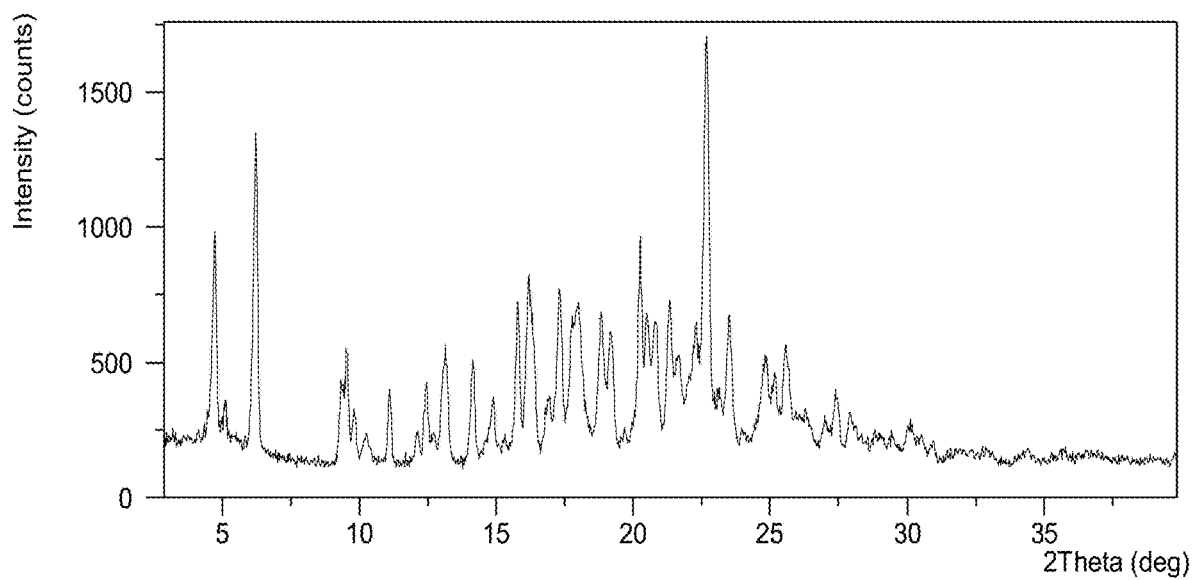
FIG. 1 shows an XRPD pattern of Form CSVI.

The present disclosure is further illustrated by the following examples which describe the preparation and use of the crystalline forms of the present disclosure in detail. It is obvious to those skilled in the art that many changes in the materials and methods can be accomplished without departing from the scope of the present disclosure.

The abbreviations used in the present disclosure are explained as follows:
XRPD: X-ray Powder Diffraction
DSC: Differential Scanning Calorimetry
TGA: Thermo Gravimetric Analysis
DVS: Dynamic Vapor Sorption
$^1$H NMR: Proton Nuclear Magnetic Resonance
HPLC: High Performance Liquid Chromatography
FaSSIF: Fasted-state simulated intestinal fluid
FeSSIF: Fed-state simulated intestinal fluid
PBS: Phosphate Buffered Saline
RPM: Revolutions Per Minute Instruments and methods used for data collection:
X-ray powder diffraction patterns in the present disclosure were acquired by a Bruker D2 PHASER X-ray powder diffractometer. The parameters of the X-ray powder diffraction method of the present disclosure are as follows:
X-Ray: Cu, Kα
Kα1 (Å): 1.54060. Kα2 (Å): 1.54439
Kα2/Kα1 intensity ratio: 0.50
Voltage: 30 (kV)
Current: 10 (mA)
Scan range (2θ): from 3.0 degree to 40.0 degree Thermo gravimetric analysis (TGA) data in the present disclosure were acquired by a TA Q500. The parameters of the TGA method of the present disclosure are as follows:
Heating rate: 10° C./min
Purge gas: nitrogen Differential scanning calorimetry (DSC) data in the present disclosure were acquired by a TA Q2000. The parameters of the DSC method of the present disclosure are as follows:
Heating rate: 10° C./min, unless otherwise specified.
Purge gas: nitrogen Dynamic Vapor Sorption (DVS) is measured via an SMS (Surface Measurement Systems Ltd.) intrinsic DVS instrument. Its control software is DVS-Intrinsic control software. Typical parameters for DVS test are as follows:
Temperature: 25° C.
Gas and flow rate: $N_2$, 200 mL/min
RH range: 0% RH to 95% RH Proton nuclear magnetic resonance spectrum data (H NMR) were collected from a Bruker Avance II DMX 400M HZ NMR spectrometer. 1-5 mg of sample was weighed and dissolved in 0.5 mL of deuterated dimethyl sulfoxide or deuterated methanol to obtain a solution with a concentration of 2-10 mg/mL.

The method parameters of stoichiometric ratio test in the resent disclosure are as follows:

| | |
|---|---|
| HPLC | Agilent 1260 with VWD |
| Column | Welch Ultimate OAA, 4.6 * 300 m |
| Mobile phase | A: 10 mM $KH_2PO_4$ aqueous solution (pH = 2.0, $H_3PO_4$) |
| | B: Acetonitrile |

-continued

| Gradient | Time (min) | % B |
|---|---|---|
| | 0.0 | 5 |
| | 15.0 | 40 |
| | 20.0 | 80 |
| | 25.0 | 80 |
| | 25.1 | 5 |
| | 35.0 | 5 |
| Running time | 35.0 min | |
| Equilibration time | 0.0 min | |
| Flow rate | 0.8 mL/min | |
| Injection volume | 5 µL | |
| Detection wavelength | UV 205 nm, 270 nm | |
| Column Temperature | 32° C. | |
| Temperature of sample tray | Room Temperature | |
| Diluent | 30% acetonitrile aqueous solution (volume ratio) | |

The method parameters of kinetic solubility test in the present disclosure are as follows:

| | |
|---|---|
| HPLC | Waters ACQUITY UPLC H-Class PLUS with PDA |
| Column | ACE Excel 3 C18, 3.0 * 100 mm, 3.0 µm |
| Mobile phase | A: 10 mM $KH_2PO_4$ aqueous solution (pH = 4.5, $H_3PO_4$) |
| | B: Acetonitrile |

| Gradient | Time (min) | % B |
|---|---|---|
| | 0.0 | 20 |
| | 1.0 | 20 |
| | 8.5 | 50 |
| | 13.0 | 80 |
| | 15.0 | 80 |
| | 16.0 | 20 |
| | 18.0 | 20 |
| Running time | 18.0 min | |
| Equilibration time | 0.0 min | |
| Flow rate | 0.5 mL/min | |
| Injection volume | 1 µL | |
| Detection wavelength | UV 210 nm | |
| Column Temperature | 40° C. | |
| Temperature of sample tray | Room Temperature | |
| Diluent | 50% acetonitrile aqueous solution (volume ratio) | |

The method parameters for related substances test in the present disclosure are as follows:

| | |
|---|---|
| HPLC | Agilent 1260 with VWD/DAD |
| Column | Waters Xbridge C18, 4.6 * 250 mm, 5.0 µm |
| Mobile phase | A: 10 mM ammonium acetate aqueous solution (pH 7.5, TEA):acetonitrile = 95:5 (v/v) |
| | B: Acetonitrile:Methanol = 70:30 (v/v) |

| Gradient | Time (min) | % B |
|---|---|---|
| | 0.0 | 20 |
| | 20.0 | 50 |
| | 35.0 | 90 |
| | 38.0 | 90 |
| | 38.1 | 20 |
| | 45.0 | 20 |
| Running time | 45.0 min | |
| Equilibrium time | 0.0 min | |
| Flow rate | 0.8 mL/min | |
| Injection volume | 5 µL | |

-continued

| | |
|---|---|
| Detection wavelength | UV 230 nm |
| Column temperature | 35° C. |
| Temperature of sample tray | Room Temperature |
| Diluent | 50% acetonitrile aqueous solution (volume ratio) |

The method parameters for drug products dissolution measurement in the present disclosure are as follows:

| | | |
|---|---|---|
| HPLC | Waters ACQUITY UPLC H-Class PLUS with PDA | |
| Column | ACE Excel 3 C18, 3.0 * 100 mm, 3.0 μm | |
| Mobile phase | A: 10 mM $KH_2PO_4$ aqueous solution (pH 4.5, $H_3PO_4$) B: Acetonitrile | |
| Gradient | Time (min) | % B |
| | 0.0 | 20 |
| | 1.0 | 20 |
| | 8.5 | 50 |
| | 13.0 | 80 |
| | 15.0 | 80 |
| | 16.0 | 20 |
| | 18.0 | 20 |
| Running time | 18.0 min | |
| Equilibration time | 0.0 min | |
| Flow rate | 0.5 mL/min | |
| Injection volume | 5 μL | |
| Detection wavelength | UV 210 nm | |
| Column Temperature | 40° C. | |
| Temperature of sample tray | Room Temperature | |
| Diluent | 50% acetonitrile aqueous solution (volume ratio) | |

According to the present disclosure, upadacitinib and/or its salt used as a raw material is solid (crystalline or amorphous), oil, liquid form or solution. Preferably, upadacitinib and/or its salt used as a raw material is a solid.

Upadacitinib and/or a salt thereof used in the following examples (corresponding to the starting materials in the examples) were prepared by known methods, for example, the method disclosed in WO2017066775A1. Unless otherwise specified, the following examples were conducted at room temperature.

EXAMPLES

Example 1 Preparation of Form CSVI 16.9 mg of upadacitinib and 9.8 mg of succinic acid were weighed into a glass vial, and 0.3 mL of isopropyl acetate/tert-butyl methyl ether (1:2, v/v) saturated with water was added. Then the sample was transferred to an oven at 35° C. and stirred for about 4 days, and another 0.2 mL of isopropyl acetate/tert-butyl methyl ether (1:2, v/v) saturated with water was added. The sample was stirred in the oven at 35° C. for about another 3 days, and a solid was obtained after isolation. The solid was stored under 40° C./75% RI open condition for about 2 days, then Form CSVI was obtained. The XRPD pattern of Form CSVI is substantially as depicted in FIG. 1, and the XRPD data are listed in Table 1.

TABLE 1

| 2θ | d spacing | Intensity % |
|---|---|---|
| 4.72 | 18.73 | 52.19 |
| 6.21 | 14.24 | 77.65 |
| 9.52 | 9.29 | 26.73 |
| 9.80 | 9.03 | 11.71 |
| 10.23 | 8.64 | 6.46 |
| 11.08 | 7.98 | 18.00 |
| 12.10 | 7.32 | 7.39 |
| 12.42 | 7.13 | 19.62 |
| 13.12 | 6.75 | 28.53 |
| 14.14 | 6.26 | 25.18 |
| 14.88 | 5.96 | 15.80 |
| 15.78 | 5.62 | 37.64 |
| 16.17 | 5.48 | 44.29 |
| 16.89 | 5.25 | 15.79 |
| 17.30 | 5.13 | 41.84 |
| 17.96 | 4.94 | 37.99 |
| 18.82 | 4.72 | 36.14 |
| 19.17 | 4.63 | 31.44 |
| 20.23 | 4.39 | 54.54 |
| 20.48 | 4.34 | 36.16 |
| 20.80 | 4.27 | 34.07 |
| 21.32 | 4.17 | 38.36 |
| 22.25 | 3.99 | 33.58 |
| 22.65 | 3.93 | 100.00 |
| 23.48 | 3.79 | 35.96 |
| 24.81 | 3.59 | 25.39 |
| 25.57 | 3.48 | 27.12 |
| 27.40 | 3.26 | 16.48 |
| 27.96 | 3.19 | 10.11 |
| 30.04 | 2.97 | 6.19 |

Example 2 Preparation of Form CSVI 1.1086 g of upadacitinib and 0.5140 g of succinic acid were weighed into a glass vial, and 19.5 mL of tert-butyl methyl ether/isopropyl alcohol/water (10:1:0.1, v/v/v) was added. The sample was stirred at 55° C. for 50 minutes, then 55.4 mg of Form CSVI seed was added. After stirring at 55° C. for another 17.5 hours, the sample was cooled to 45° C. and stirred for 1 hour.

Figure 2:
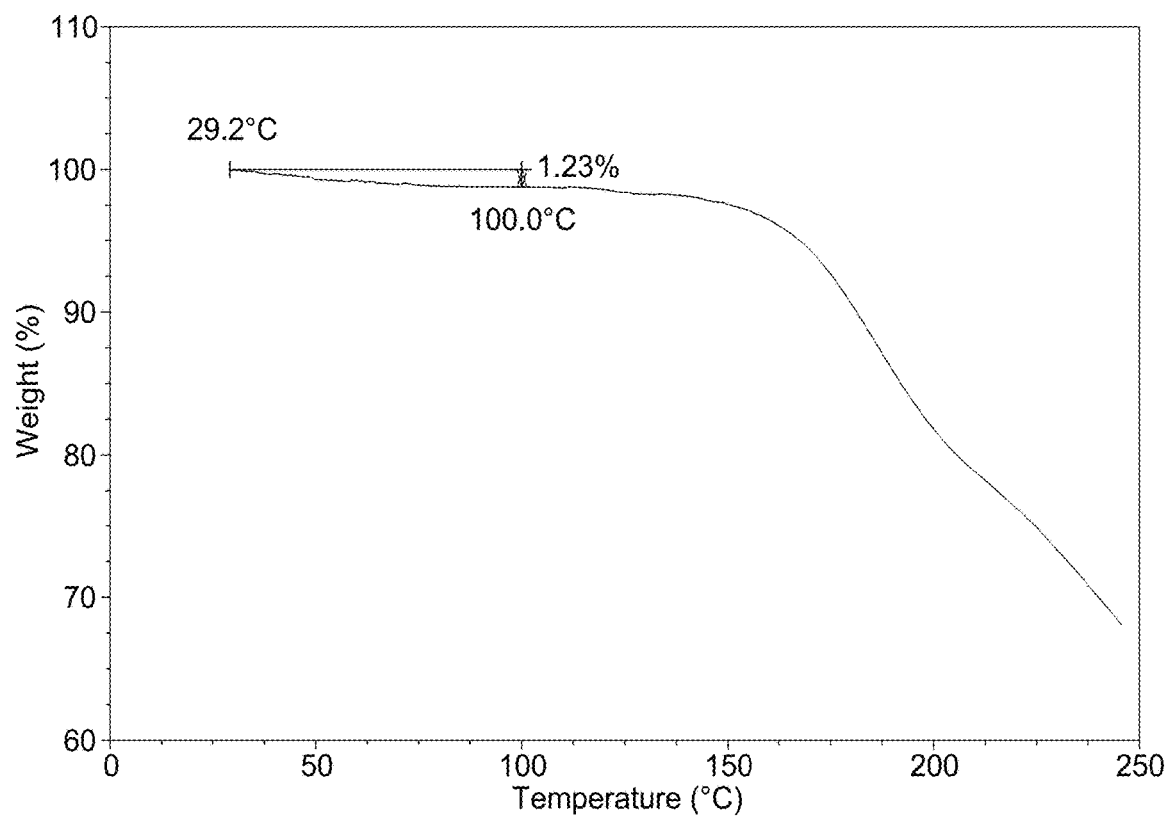
FIG. 2 shows a TGA curve of Form CSVI.

Then the sample was cooled to 40° C. and stirred for 190 minutes, then cooled to 35° C. and stirred for 280 minutes, and cooled to 25° C. and stirred for 1 day. Another 1.0 mL of tert-butyl methyl ether/isopropyl alcohol/water (10:1:0.1, v/v/v) and 3.0 mL of n-heptane were added, and the sample was stirred at 25° C. for about 4 days. Another 5.0 mL of n-heptane was added, and the solid was isolated after stirring at 25° C. for another 5 hours (The temperature of all the above procedures was controlled by a hotplate stirrer). The isolated solid was vacuum dried at 75° C. for about 17.5 hours and placed under 40° C./75% RH in open condition for about 5 days, then Form CSVI was obtained. The TGA curve of Form CSVI shows about 1.2% weight loss when heated to 100° C., which is substantially as depicted in FIG. 2. The molar ratio of succinic acid to upadacitinib in Form CSVI is 0.79:1 determined by $^1$H NMR.

Figure 3:
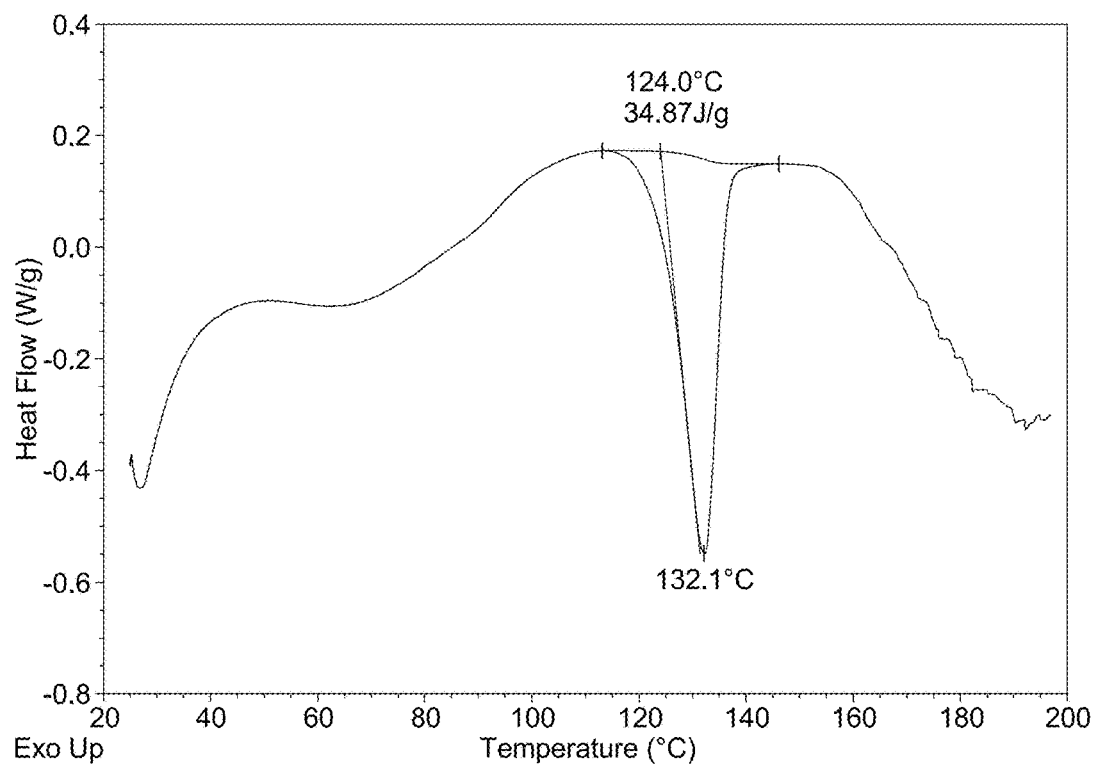
FIG. 3 shows a DSC curve of Form CSVI.

Example 3 Preparation of Form CSVI 1.0236 g of upadacitinib and 0.2796 g of succinic acid were dissolved in 6 mL of n-propanol, and the solution was filtered into a jacketed reactor whose temperature was 60° C. After mechanical stirring for about 5-10 minutes, 10 mL of n-heptane was added slowly. 0.0500 g of Form CSVI was weighed and dispersed evenly in 2 mL of n-heptane. Next the suspension was added into the reactor. The system was aged at 60° C. for about 1 hour and cooled to 35° C. (in 5 hours). After aging at 35° C. for about 13 hours, 18 mL of n-heptane was added drop by drop (taking 3 hours) and the system was aged for another hour. The system was cooled to 5° C. (taking 3 hours) and aged for about 15 hours. The wet cake obtained by filtration was dried at room temperature for about 9 hours, followed by vacuum drying in oven at 75° C. for about 38 hours. The dried solid was jet milled (the feeding pressure is 0.3 MPa, the milling pressure is 0.1 MPa) and vacuum dried in oven at 75° C. for about 23 hours, then Form CSVI was obtained. The DSC curve of Form CSVI is substantially as depicted in FIG. 3, and one endothermic peak appears at around 124° C. (onset temperature). The molar ratio of succinic acid to upadacitinib in Form CSVI is 0.63:1 determined by HPLC.

Example 4 Preparation of Form CSVI 1.0237 g of upadacitinib and 0.3413 g of succinic acid were dissolved in 6 mL of n-propanol, and the solution was filtered into a jacketed reactor whose temperature was 60° C. After mechanical stirring for about 5-10 minutes, 10 mL of n-heptane was added slowly. 0.0500 g of Form CSVI was weighed then dispersed evenly in 2 mL of n-heptane, next the suspension was added into the reactor. The system was aged at 60° C. for about 1 hour and cooled to 35° C. (taking 5 hours). After aging at 35° C. for about 13 hours, 18 mL of n-heptane was added drop by drop (taking 3 hours) and the system was aged for another hour. The reaction mass was cooled to 5° C. (taking 3 hours) and aged for about 15 hours. The wet cake obtained by filtration was dried at room temperature for about 9 hours, followed by vacuum drying in oven at 75° C. for about 38 hours. The dried solid was jet milled (the feeding pressure was 0.3 MPa, the milling pressure was 0.1 MPa) and vacuum dried in oven at 75° C. for about 23 hours, then Form CSVI was obtained. The molar ratio of succinic acid to upadacitinib in Form CSVI is 0.85:1 determined by HPLC.

Example 5 Kinetic Solubility of Form CSVI

The solubility of Form C is disclosed in WO2017066775A1. Approximately 15-30 mg of Form CSVI in the present disclosure was suspended into 1.8 mL of FeSSIF, 1.8 mL of FaSSIF and 1.8 mL of pH=7.4 PBS. After equilibration for 24 hours and 48 hours, the concentration of upadacitinib in saturated solutions were tested by HPLC and the results are listed in Table 2.

TABLE 2

| | Solubility | | |
|---|---|---|---|
| | Form C (mg/mL) | Form CSVI (mg/mL) | |
| Media | 24-48 hours | 24 hours | 48 hours |
| FeSSIF (pH 5.0, 37° C.) | 0.47 | 2.20 | 2.22 |
| FaSSIF (pH 6.5, 37° C.) | 0.22 | 1.87 | 1.71 |
| pH 7.4, 25° C. | 0.19 | 0.88 | 0.85 |

The results show that Form CSVI has higher solubility in FeSSIF, FaSSIF and pH=7.4 PBS.

Example 6 Stability of Form CSVI

Figure 4:
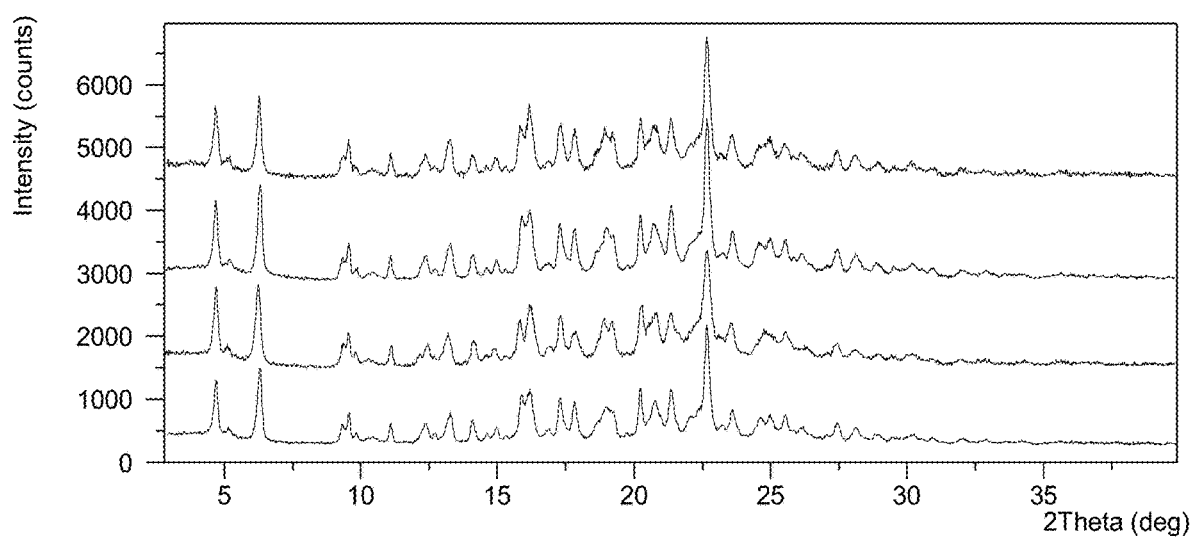
FIG. 4 shows an XRPD pattern overlay of Form CSVI before and after storage (from top to bottom: Initial, stored at 40° C./75% RH (sealed) for six months, stored at 40° C./75% RH (open) for six months, stored at 60° C./75% RH (sealed) for one month).

Approximately 5 mg of Form CSVI in the present disclosure was stored under 40° C./75% RH and 60° C./75% RH conditions. The purity and crystalline form were tested before and after storage by HPLC and XRPD. The results are listed in Table 3 and the XRPD overlay is substantially as depicted in FIG. 4.

TABLE 3

| Condition | | Time | Solid form | Purity |
|---|---|---|---|---|
| Initial | | — | Form CSVI | 99.89% |
| 40° C./75% RH | Sealed | 6 months | Form CSVI | 99.92% |
| | Open | 6 months | Form CSVI | 99.89% |
| 60° C./75% RH | Sealed | 1 month | Form CSVI | 99.91% |

Figure 5:
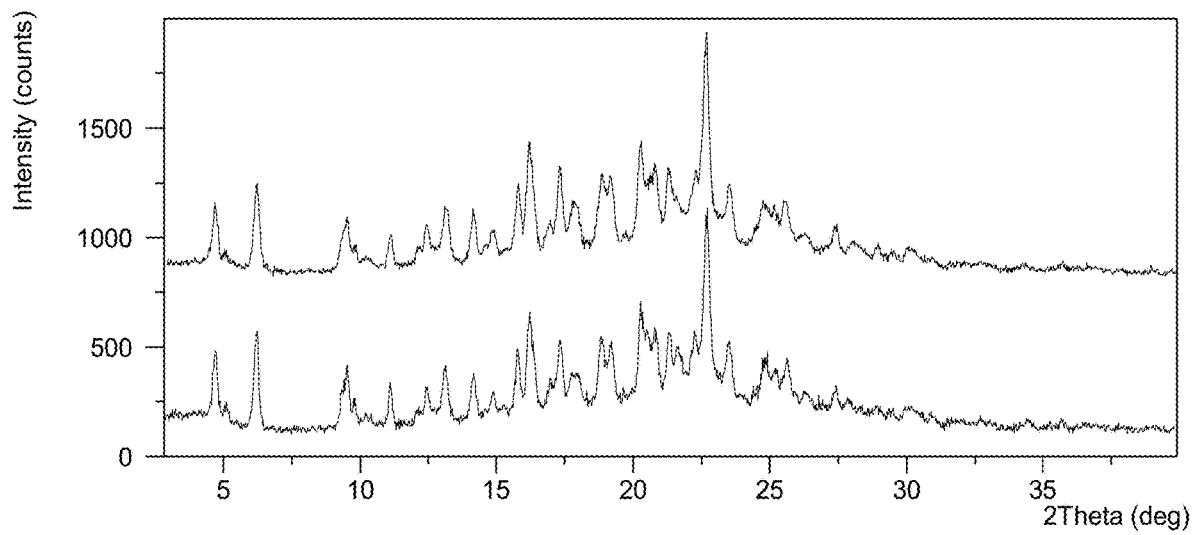
FIG. 5 shows an XRPD pattern overlay of Form CSVI before and after DVS (top: initial, bottom: after DVS).

The results show that Form CSVI is stable for at least 6 months under 40° C./75% RH (sealed) and 40° C./75% RH (open) conditions. It can be seen that Form CSVI has good stability under accelerated conditions. Form CSVI is stable for at least 1 month under 60° C./75% RH (sealed) condition. It can be seen that Form CSVI has good stability under more stressed condition as well. Approximately 10 mg of Form CSVI in the present disclosure underwent a humidity cycle of 0% RH-95% RH-0% RH with a dynamic vapor sorption (DVS) analyzer. The crystalline form before and after humidity cycle was tested by XRPD and the results are shown in FIG. 5. The results show that no form change is observed after DVS test, indicating Form CSVI has good stability under both high and low relative humidity.

Example 7 Preparation of Form CSVII 16.3 mg of upadacitinib and 11.5 mg of adipic acid were weighed into a glass vial, and 0.3 mL of isopropyl acetate/tert-butyl methyl ether (1:3, v/v) was added. The sample was transferred to an oven at 35° C. and stirred for about 4 days. Another 0.2 mL of isopropyl acetate/tert-butyl methyl ether (1:3, v/v) was added. The sample was stirred in an oven at 35° C. for about another 3 days, and then stirred at room temperature for 6 days. A solid was obtained after isolation. After vacuum drying at 30° C. overnight, Form CSVII was obtained.

Figure 6:
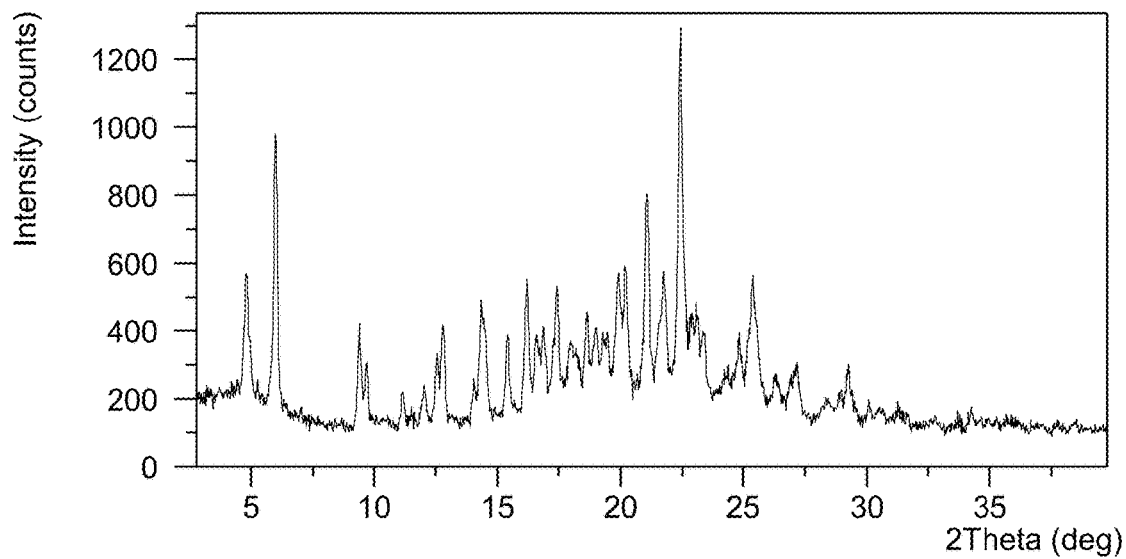
FIG. 6 shows an XRPD pattern of Form CSVII in Example 9.
Figure 7:
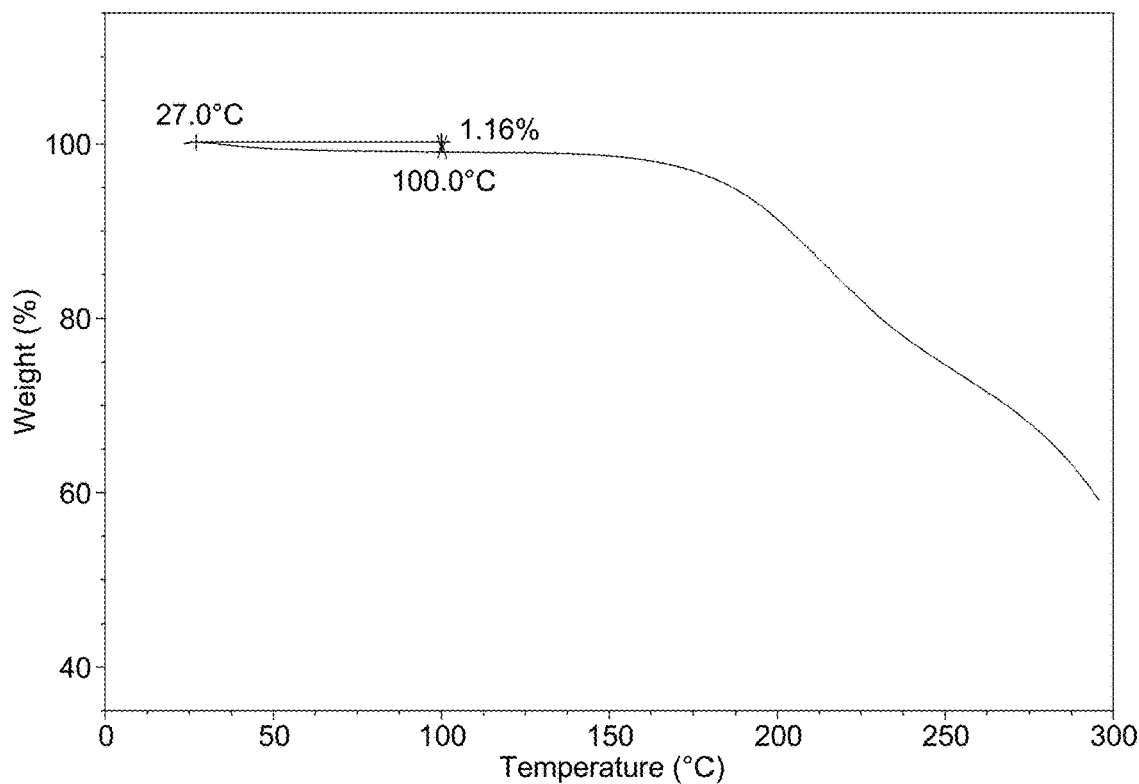
FIG. 7 shows a TGA curve of Form CSVII in Example 9.

Example 8 Preparation of Form CSVII 195.8 mg of upadacitinib and 158.8 mg of adipic acid were weighed into a glass vial, and 5 mL of isopropyl acetate/tert-butyl methyl ether (1:2, v/v) was added. The sample was stirred at room temperature overnight, and 10.1 mg of Form CSVII seed was added. The sample was stirred at room temperature for about another 5 days. A solid was obtained after isolation and vacuum dried at 35° C. for 2.5 hours. 150.9 mg of the obtained solid was weighed into a glass vial, and 3.0 mL of tert-butyl methyl ether saturated with water was added. The sample was stirred at room temperature for about 2 days, and a solid was obtained by isolation. 25.4 mg of the solid obtained was placed under 40° C./75% RH condition for about 1 day, and Form CSVII was obtained. The XRPD pattern of Form CSVII is substantially as depicted in FIG. 6, and the XRPD data are listed in Table 4. The TGA curve of Form CSVII shows about 1.2% weight loss when heated to 100° C., which is substantially as depicted in FIG. 7.

TABLE 4

| 2θ | d spacing | Intensity % |
|---|---|---|
| 4.79 | 18.45 | 34.78 |
| 5.98 | 14.78 | 72.97 |
| 9.38 | 9.43 | 27.03 |
| 9.66 | 9.15 | 16.57 |
| 11.14 | 7.94 | 8.58 |
| 12.01 | 7.37 | 10.03 |
| 12.54 | 7.06 | 19.36 |

TABLE 4-continued

| 2θ | d spacing | Intensity % |
|---|---|---|
| 12.79 | 6.92 | 26.60 |
| 14.34 | 6.17 | 32.86 |
| 15.40 | 5.75 | 24.28 |
| 16.18 | 5.48 | 36.97 |
| 16.59 | 5.34 | 22.65 |
| 16.87 | 5.26 | 25.41 |
| 17.40 | 5.10 | 36.40 |
| 18.04 | 4.92 | 20.46 |
| 18.63 | 4.76 | 29.55 |
| 18.98 | 4.68 | 25.75 |
| 19.36 | 4.59 | 22.32 |
| 19.89 | 4.46 | 38.85 |
| 20.18 | 4.40 | 41.39 |
| 21.05 | 4.22 | 60.95 |
| 21.74 | 4.09 | 39.11 |
| 22.40 | 3.97 | 100.00 |
| 23.38 | 3.81 | 24.23 |
| 24.82 | 3.59 | 23.56 |
| 25.37 | 3.51 | 38.77 |
| 26.31 | 3.39 | 12.78 |
| 27.12 | 3.29 | 14.86 |
| 29.22 | 3.06 | 15.27 |
| 31.31 | 2.86 | 4.28 |
| 34.23 | 2.62 | 3.34 |

Example 9 Preparation of Form CSVII 1.0001 g of upadacitinib and 0.4228 g of adipic acid were dissolved with 6 mL of n-propanol/n-butanol (3:1, v/v), then the solution was filtered into a reactor for mechanical stirring. After the temperature of the reactor was raised to 60° C., 10 mL of n-heptane was added slowly. 0.1018 g of Form CSVII was dispersed evenly in 2 mL of n-heptane, and the suspension was added into the reactor slowly. After aging at 60° C. for 2 hours, the reaction mass was cooled to 35° C. (taking 8 hours) and aged for another 5.5 hours. The suspension was filtered, and the wet cake was washed with n-heptane. The wet cake was transferred to vacuum drying at 75° C. for about 16 hours, then Form CSVII was obtained. The molar ratio of adipic acid to upadacitinib in Form CSVII is 0.65:1 determined by $^1$H NMR.

Example 10 Preparation of Form CSVII 0.9997 g of upadacitinib and 0.4611 g of adipic acid were dissolved with 6 mL n-propanol/n-butanol (3:1, v/v), then the solution was filtered into a 50 mL reactor for mechanical stirring. After the temperature of reactor was raised to 60° C., 10 mL of n-heptane was added slowly. 0.1018 g of Form CSVII was suspended in 2 mL of n-heptane at room temperature, and the suspension was added into the reactor slowly. After aging at 60° C. for 2 hours, the reaction mass was cooled to 35° C. (taking 8 hours) and aged for another 5.5 hours. The suspension was filtered, and the wet cake was washed with n-heptane. The wet cake was transferred to vacuum drying at 75° C. for about 16 hours, then Form CSVII was obtained. The molar ratio of adipic acid to upadacitinib in Form CSVII is 0.77:1 determined by $^1$H NMR.

Figure 8:
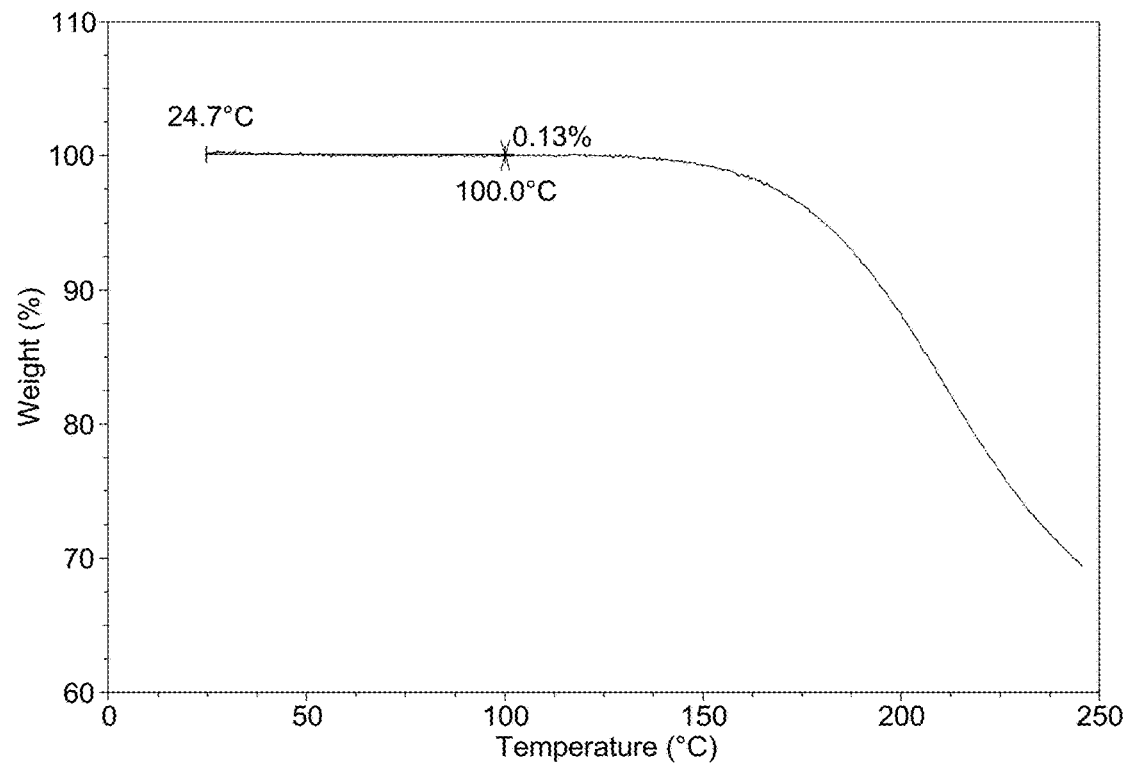
FIG. 8 shows a TGA curve of Form CSVII in Example 11.
Figure 9:
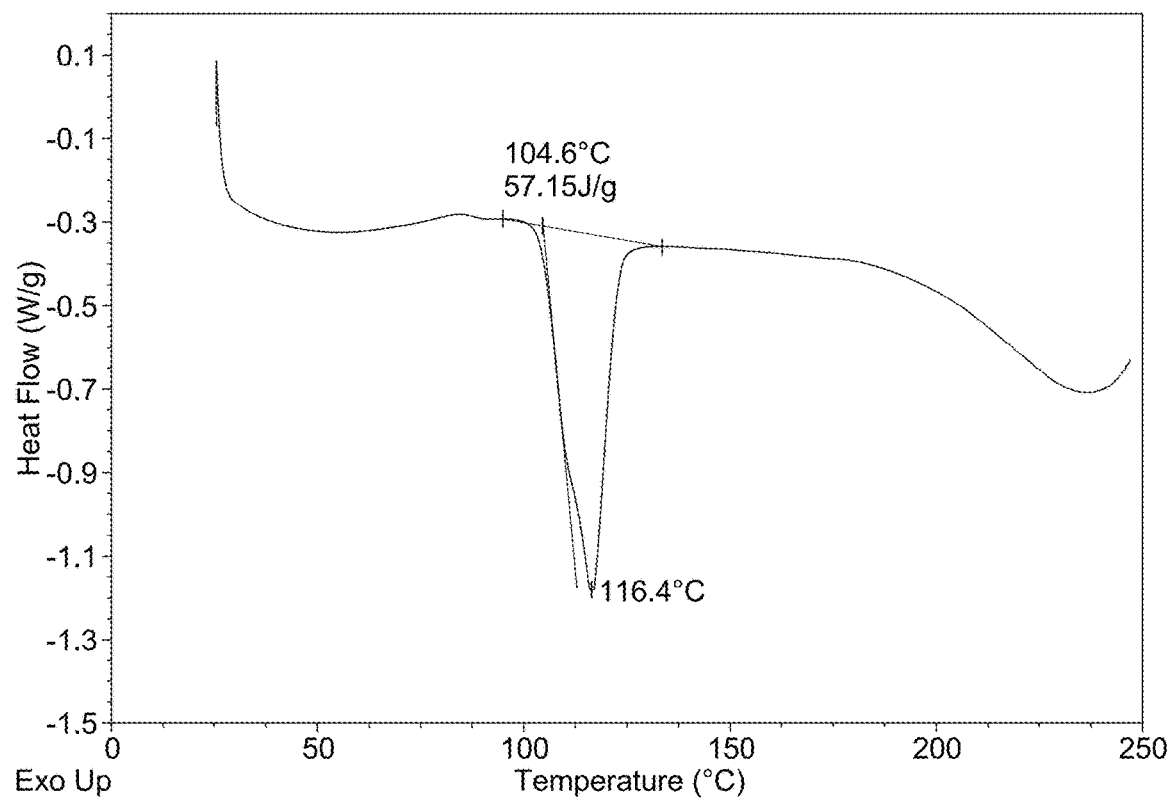
FIG. 9 shows a DSC curve of Form CSVII in Example 11.

Example 11 Preparation of Form CSVII 501.2 mg of upadacitinib and 230.2 mg of adipic acid were weighed into a 50 ml reactor, and 20 mL of iso-butanol/n-heptane (1:3, v/v) was added. The system was mechanically stirred, and a clear solution was obtained when the temperature was raised up to 75° C. The system was cooled to 55° C. and aged for 0.5 hour, then cooled to 45° C. and aged for 0.5 hour. Approximately 5 mg of Form CSVII was dispersed evenly in about 0.2 mL of iso-butanol/n-heptane (1:3, v/v), and the suspension was added into the reactor slowly. After aging for about 2 hours, the system was cooled to 25° C. (taking 4 hours) and aged for about 85 hours. The suspension was filtered, and the wet cake was washed with the filtrate. The wet cake was vacuum dried at 50° C. for about 24 hours and followed by drying at room temperature for about 8.5 hours. Then the solid was vacuum dried at 75° C. in an oven for about 15 hours, and Form CSVII was obtained. The TGA curve of Form CSVII shows about 0.1% weight loss when heated to 100° C., which is substantially as depicted in FIG. 8. The DSC curve of Form CSVII is substantially as depicted in FIG. 9, and one endothermic peak appears at around 105° C. (onset temperature). The molar ratio of adipic acid to upadacitinib in Form CSVII is 0.99:1 determined by $^1$H NMR.

Example 12 Kinetic Solubility of Form CSVII

The solubility of Form C is disclosed in WO2017066775A1. Approximately 15-30 mg of Form CSVII in the present disclosure was suspended into 1.8 mL of FeSSIF, 1.8 mL of FaSSIF and 1.8 mL of pH=7.4 PBS. After equilibration for 24 hours and 48 hours, the concentration of upadacitinib in saturated solutions was tested by HPLC and the results are listed in Table 5.

TABLE 5

| | Solubility | | |
|---|---|---|---|
| | Form C (mg/mL) | Form CSVII (mg/mL) | |
| Media | 24-48 hours | 24 hours | 48 hours |
| FeSSIF (pH 5.0, 37° C.) | 0.47 | 2.28 | 2.47 |
| FaSSIF (pH 6.5, 37° C.) | 0.22 | 2.02 | 2.17 |
| pH 7.4, 25° C. | 0.19 | 0.92 | 0.85 |

The results show that Form CSVII has higher solubility in FeSSIF, FaSSIF and pH=7.4 PBS.

Example 13 Stability of Form CSVII

Figure 10:
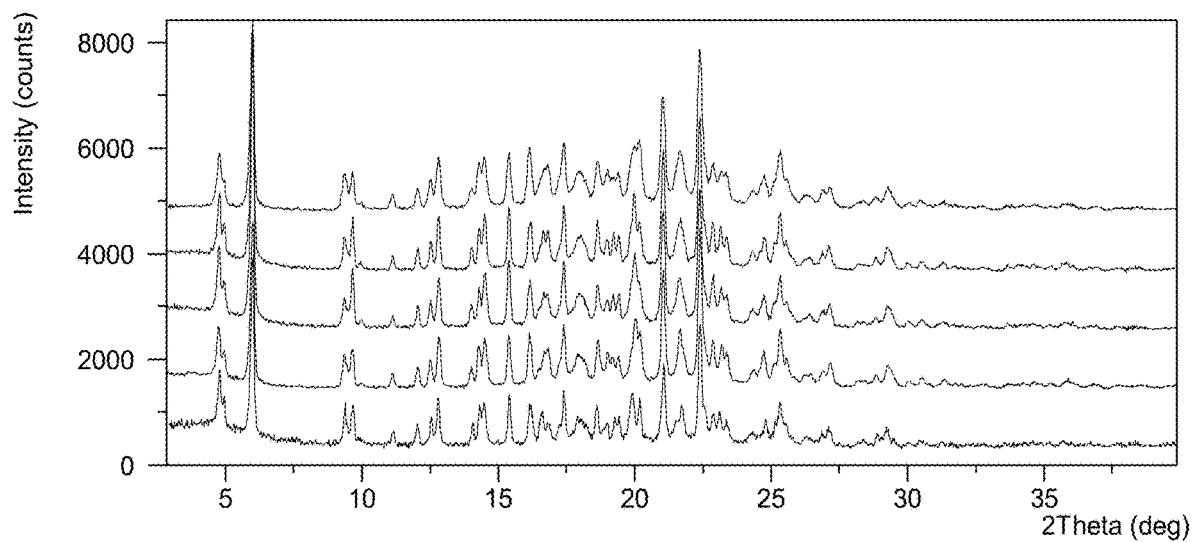
FIG. 10 shows an XRPD pattern overlay of Form CSVII before and after storage (from top to bottom: Initial, stored at 25° C./60% RH (sealed) for six months, stored at 25° C./60% RH (open) for six months, stored at 40° C./75% RH (sealed) for six months, stored at 60° C./75% RH (sealed) for one month).

Approximately 5 mg of Form CSVII in the present disclosure was stored under 25° C./60% RH, 40° C./75% RH and 60° C./75% RH conditions. The purity and crystalline form were tested before and after storage by HPLC and XRPD. The results are listed in Table 6 and the XRPD overlay is substantially as depicted in FIG. 10.

TABLE 6

| Condition | | Time | Solid form | Purity |
|---|---|---|---|---|
| Initial | | — | Form CSVII | 99.92% |
| 25° C./60% RH | Sealed | 6 months | Form CSVII | 99.92% |
| | Open | 6 months | Form CSVII | 99.91% |
| 40° C./75% RH | Sealed | 6 months | Form CSVII | 99.92% |
| 60° C./75% RH | Sealed | 1 month | Form CSVII | 99.92% |

The results show that Form CSVII is stable for at least 6 months under 25° C./60% RH and 40° C./75% RH (sealed) conditions. It can be seen that Form CSVII has good stability under long-term and accelerated conditions. Form CSVII is stable for at least 1 month under 60° C./75% RH (sealed) condition. It can be seen that Form CSVII has good stability under more stressed condition as well.

Figure 11:
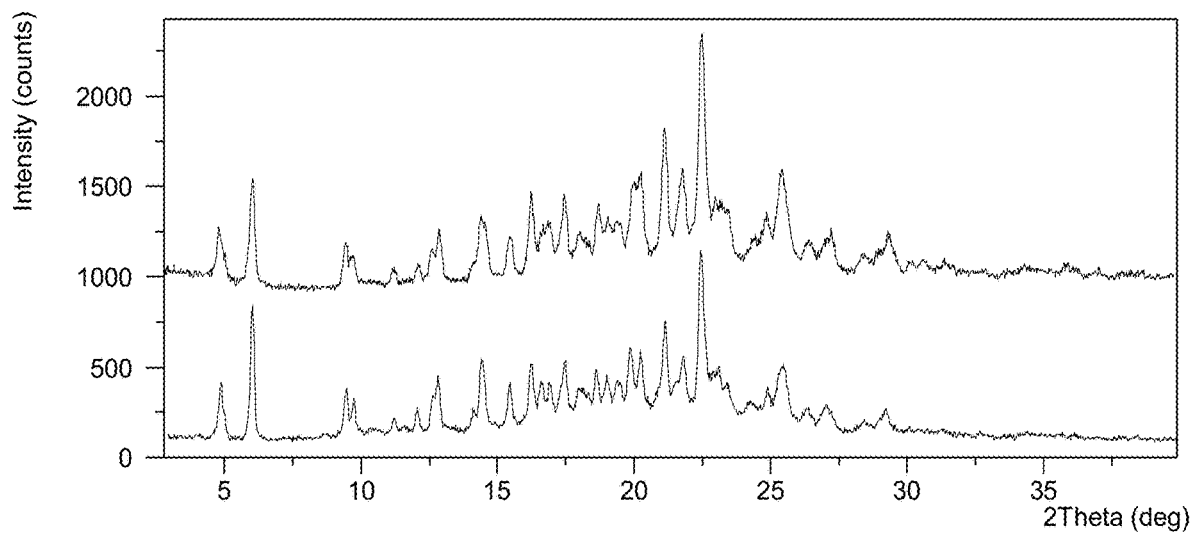
FIG. 11 shows an XRPD pattern overlay of Form CSVII before and after DVS (top: initial, bottom: after DVS).

Approximately 10 mg of Form CSVII in the present disclosure underwent a humidity cycle of 0% RH-95% RH-0% RH with a dynamic vapor sorption (DVS) analyzer. The crystalline form before and after humidity cycle was tested by XRPD and the results are shown in FIG. 11. The results show that no form change is observed before and after DVS test, indicating Form CSVII has good stability under both high and low relative humidity.

Example 14 Preparation of Drug Product

Figure 12:
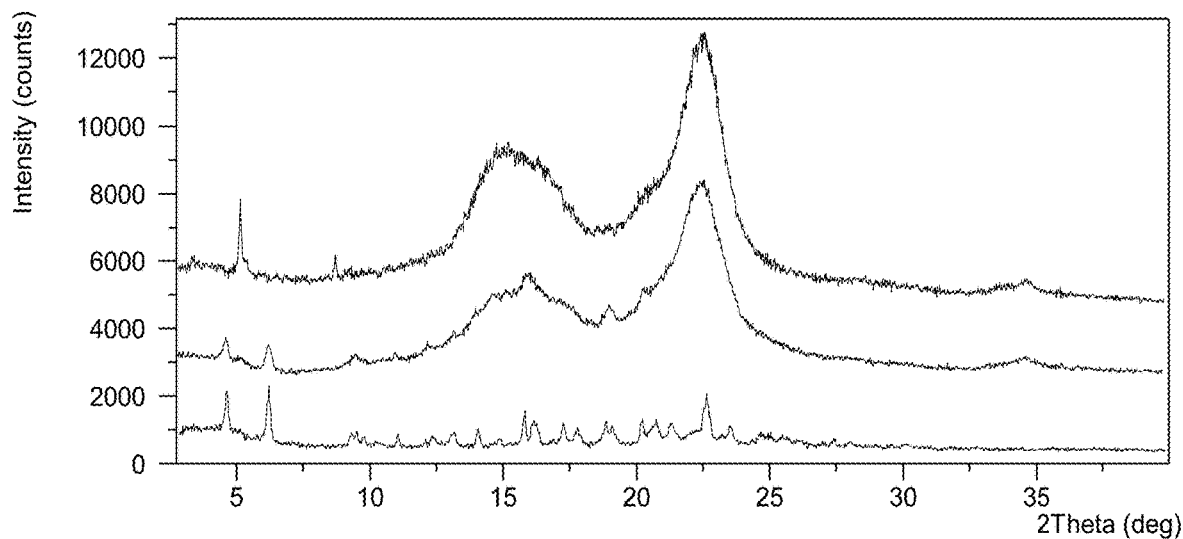
FIG. 12 shows an XRPD pattern overlay of Form CSVI during production process (from top to bottom: excipient blend, Form CSVI drug product, Form CSVI).
Figure 13:
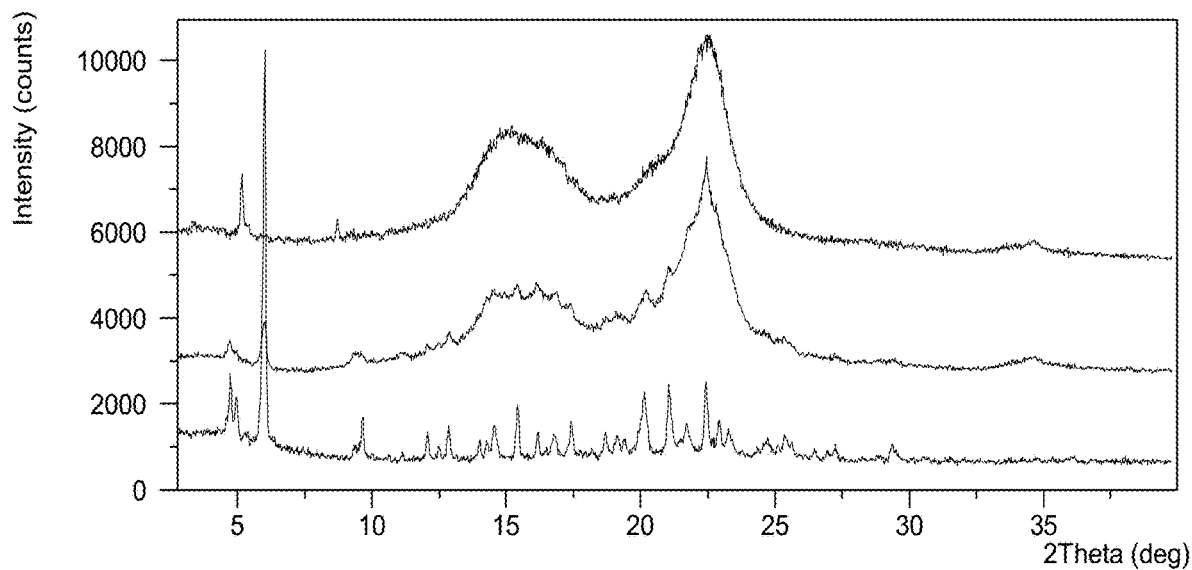
FIG. 13 shows an XRPD pattern overlay of Form CSVII during production process (from top to bottom: excipient blend, Form CSVII drug product, Form CSVII).

The formulation and preparation process of Form CSVI, Form CSVII and Form C are shown in Table 7 and Table 8. The XRPD overlays before and after formulation process are shown in FIG. 12 (Form CSVI) and FIG. 13 (Form CSVII), indicating Form CSVI and Form CSVII are physically stable after formulation procedure.

TABLE 7

| No. | Component | mg/unit | % (w/w) | Function |
|---|---|---|---|---|
| 1 | Crystalline upadacitinib* | 20.0 | 20.0 | API |
| 2 | Microcrystalline cellulose (Avicel PH 102) | 70.0 | 70.0 | Filler |
| 3 | Crospovidone (Polyplasdone XL) | 9.0 | 9.0 | Disintegrant |
| 4 | Magnesium stearate (SH-YM-M) | 1.0 | 1.0 | Lubricant |

Remark:
*The formulations are the same except for different solid forms of upadacitinib (Form CSVI, Form CSVII and Form C). 20 mg corresponds to the mass of upadacitinib free base, and the weight of different solid forms needs to be re-calculated accordingly.

TABLE 8

| Stage | Procedure |
|---|---|
| Pre-blending | According to the formulation, No. 1-4 materials were weighed into an LDPE bag and manually blended for 2 minutes. |
| Sifting | The mixture was sieved through a 35-mesh sieve and then put in an LDPE bag and blended manually for 1 minute. |
| Simulation of dry granulation | The mixture was pressed by a single punch manual tablet press (type: ENERPAC, die: φ 20 mm round, tablet weight: 500 mg ± 20 mg, pressure: 5 ± 1 KN). The flakes were pulverized by mortar and sieved through a 20-mesh sieve. |
| Tableting | The mixture was tableted by a single punch manual tablet press (type: ENERPAC; die: φ7 mm round; tablet weight: 100 mg ± 2 mg; pressure: 5 ± 1 KN). |
| Package | The tablets were packed in 35 cc HDPE bottles, with one tablet and 1 g of desiccant per bottle. |

Example 15 Stability of the Formulation

The tablets of Form CSVI and Form CSVII obtained in example 14 were packed in HDPE bottles with 1 g of desiccant and stored under 25° C./60% RH and 40° C./75% RH conditions. Crystalline form and impurity of the samples were tested, and the results were listed in Table 9. The results indicate that drug products of Form CSVI and Form CSVII can keep stable under 25° C./60% RH and 40° C./75% RH conditions for at least 3 months, and the purity remains basically unchanged.

TABLE 9

Figure 14:
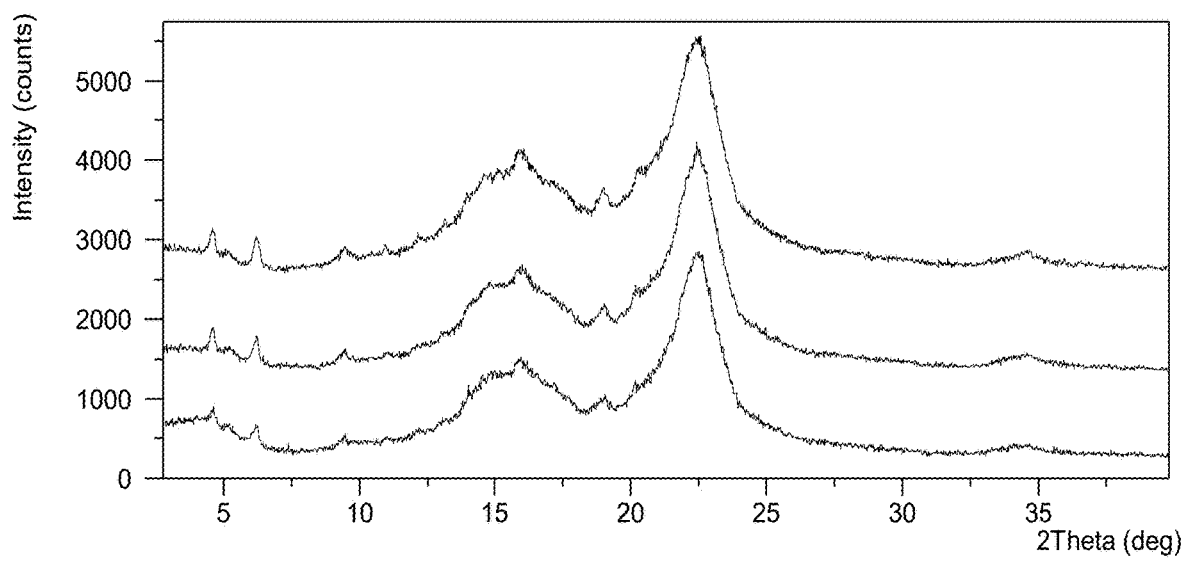
FIG. 14 shows an XRPD pattern overlay of Form CSVI drug product from stability test (from top to bottom: Initial, stored at 25° C./60% RH (sealed, 1 g of desiccant) for three months, stored at 40° C./75% RH (sealed, 1 g of desiccant) for three months).
Figure 15:
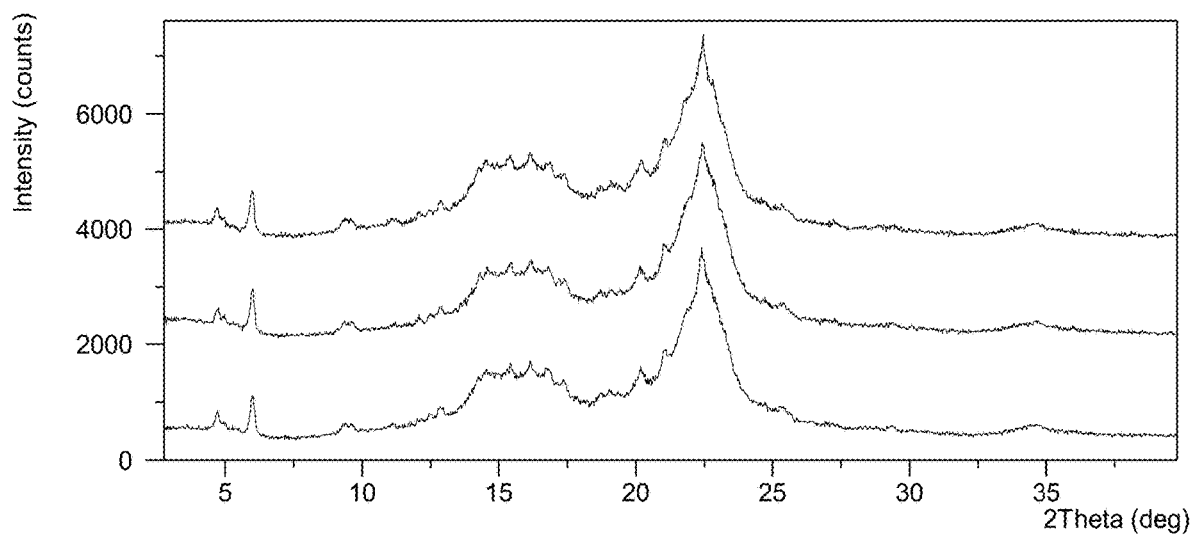
FIG. 15 shows an XRPD pattern overlay of Form CSVII drug product from stability test (from top to bottom: Initial, stored at 25° C./60% RH (sealed, 1 g of desiccant) for three months, stored at 40° C./75% RH (sealed, 1 g of desiccant) for three months).

| Solid form | Condition | Time | Solid form | Purity | FIGS. |
|---|---|---|---|---|---|
| Form CSVI | Initial | — | Form CSVI | 99.93% | FIG. 14 |
| | 25° C./60% RH | 3 months | Form CSVI | 99.90% | |
| | 40° C./75% RH | 3 months | Form CSVI | 99.87% | |
| Form CSVII | Initial | — | Form CSVII | 99.31% | FIG. 15 |
| | 25° C./60% RH | 3 months | Form CSVII | 99.32% | |
| | 40° C./75% RH | 3 months | Form CSVII | 99.33% | |

Example 16 Dissolution of Form CSVI

Figure 16:
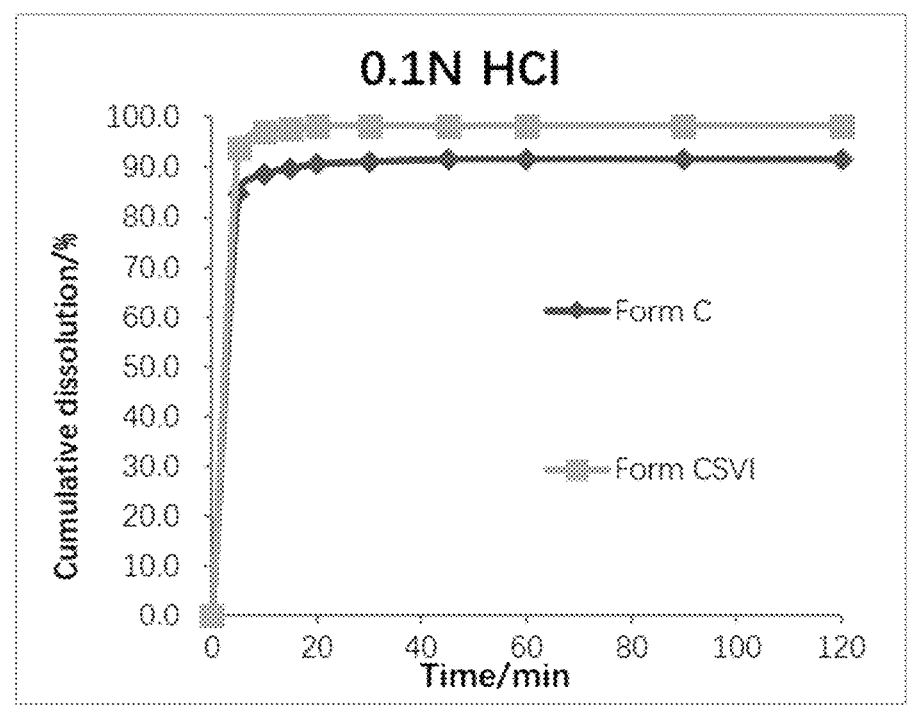
FIG. 16 shows dissolution curves of Form CSVI drug product and Form C drug product in 0.1 N HCl.

Dissolution tests were performed on Form CSVI drug product and Form C drug product obtained from example 14, and the method and parameters are listed in Table 10. The dissolution data of Form CSVI drug product are presented in Table 11 and FIG. 16, indicating that the cumulative drug release of Form CSVI at 30 minutes is higher than 85%, which meets the standards of rapid dissolution. Meanwhile, the dissolution rate of Form CSVI is higher than that of Form C in 0.1 N HC, and the bioavailability in vivo of Form CSVI is speculated to be superior to that of Form C.

TABLE 10

| Instrument | Sotax AT7 |
|---|---|
| Method | Paddle |
| Strength | 20 mg |
| Volume of medium | 900 mL |
| Speed | 50 rpm |
| Temperature of medium | 37° C. |
| Sampling Time | 0.1N HCl: 5, 10, 15, 20, 30, 45, 60, 90, 120 min |
| Supplement medium | No (1 mL was sampled at each time point) |

TABLE 11

| | Medium 0.1N HCl Cumulative drug release (%) | |
|---|---|---|
| Time (min) | Form C | Form CSVI |
| 0 | 0.0 | 0.0 |
| 5 | 85.0 | 93.8 |
| 10 | 88.6 | 97.2 |
| 15 | 89.8 | 97.8 |
| 20 | 90.7 | 98.3 |
| 30 | 91.1 | 98.5 |
| 45 | 91.6 | 98.3 |
| 60 | 91.7 | 98.5 |
| 90 | 91.7 | 98.4 |
| 120 | 91.6 | 98.4 |

Example 17 Dissolution of Form CSVII

Figure 17:
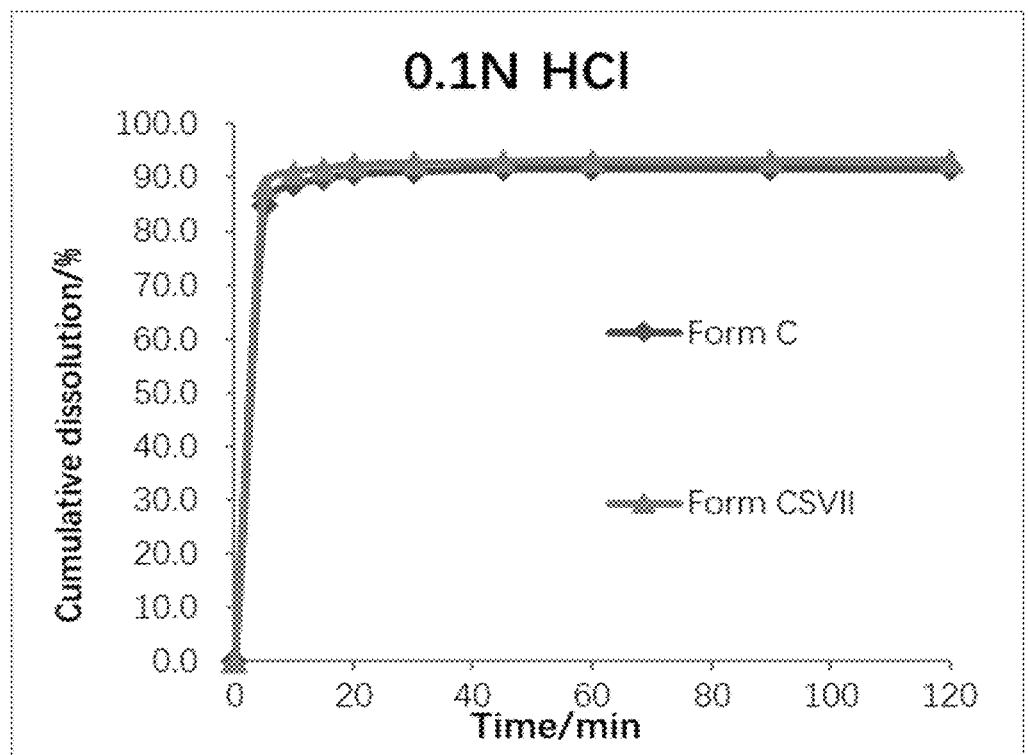
FIG. 17 shows dissolution curves of Form CSVII drug product and Form C drug product in 0.1 N HCl.
Figure 18:
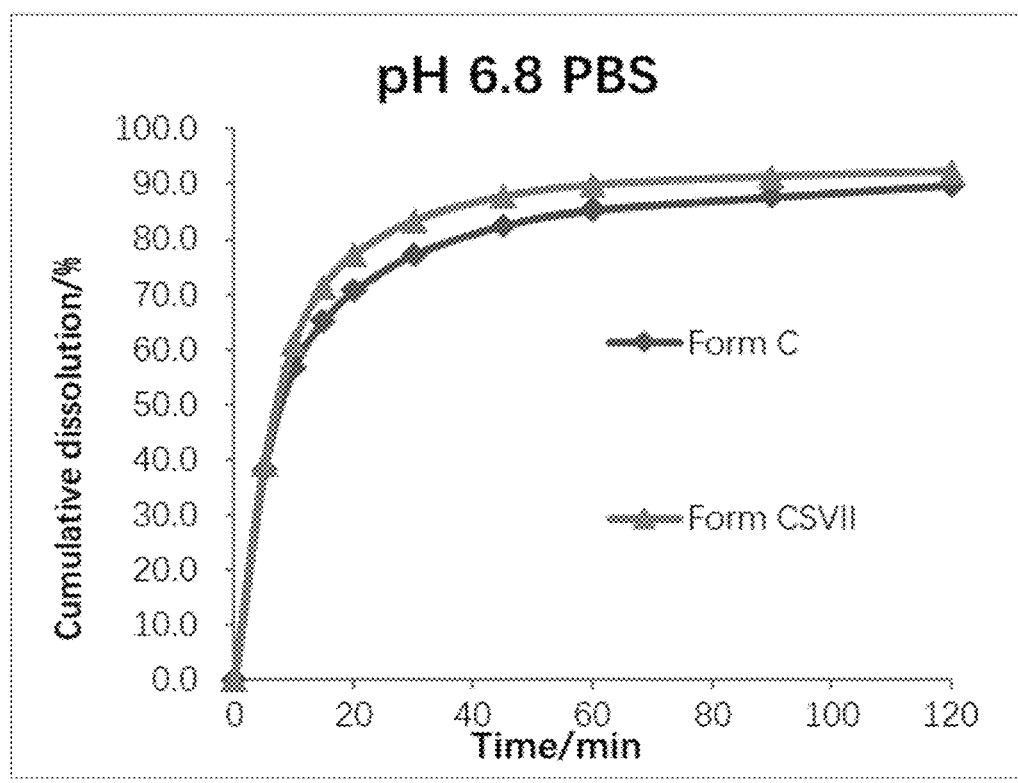
FIG. 18 shows dissolution curves of Form CSVII drug product and Form C drug product in pH 6.8 PBS.

Dissolution tests were performed on Form CSVII drug product and Form C drug product obtained from example 14, and the test method is listed in Table 12. The dissolution data of Form CSVII drug product are presented in Table 13-14 and FIG. 17-18, indicating that the accumulative drug release of Form CSVII in 0.1 N HCl at 30 minutes is higher than 85%, which meets the standards of rapid dissolution. Meanwhile, the dissolution rate of Form CSVII is higher than that of Form C in both 0.1 N HCl and pH6.8 PBS, and the bioavailability in vivo of Form CSVII is speculated to be superior to that of Form C.

TABLE 12

| Instrument | Sotax AT7 |
|---|---|
| Method | Paddle |
| Strength | 20 mg |
| Volume of medium | 900 mL |
| Speed | 50 rpm |
| Temperature of medium | 37° C. |
| Sampling Time | 5, 10, 15, 20, 30, 45, 60, 90, 120 min |
| Supplement medium | No (1 mL was sampled at each time point) |

TABLE 13

| | Medium 0.1N HCl Cumulative drug release (%) | |
|---|---|---|
| Time (min) | Form C | Form CSVII |
| 0 | 0.0 | 0.0 |
| 5 | 85.0 | 88.3 |
| 10 | 88.6 | 91.0 |
| 15 | 89.8 | 91.7 |
| 20 | 90.7 | 92.4 |
| 30 | 91.1 | 92.7 |
| 45 | 91.6 | 93.0 |
| 60 | 91.7 | 93.1 |
| 90 | 91.7 | 93.1 |
| 120 | 91.6 | 93.2 |

TABLE 14

| | Medium pH 6.8 PBS Cumulative drug release (%) | |
|---|---|---|
| Time (min) | Form C | Form CSVII |
| 0 | 0.0 | 0.0 |
| 5 | 38.2 | 39.1 |
| 10 | 56.7 | 61.0 |
| 15 | 65.1 | 71.4 |
| 20 | 70.6 | 77.1 |
| 30 | 77.3 | 83.4 |
| 45 | 82.6 | 87.6 |
| 60 | 85.3 | 89.7 |
| 90 | 87.7 | 91.3 |
| 120 | 89.8 | 92.2 |

The examples described above are only for illustrating the technical concepts and features of the present disclosure and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

We claim:

1. A crystalline form CSVI of upadacitinib, wherein crystalline form CSVI is a co-crystal of upadacitinib and succinic acid

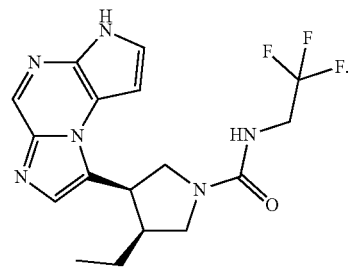 [SMILES: CC[C@@H]1CN(C(=O)NCC(F)(F)F)C[C@@H]1c1cnc2cnc3[nH]ccc3n12]

2. The crystalline form CSVI according to claim 1, wherein the crystalline form CSVI exhibits an X-ray powder diffraction pattern comprising one or two or three characteristic peaks at 2theta values of 4.7°±0.2°, 6.2°±0.2° and 22.7°±0.2° using CuKα radiation.

3. The crystalline form CSVI according to claim 1, wherein the crystalline form CSVI exhibits an X-ray powder diffraction pattern comprising one or two or three characteristic peaks at 2theta values of 15.8°±0.2°, 17.3°±0.2° and 23.5°±0.2° using CuKα radiation.

4. The crystalline form CSVI according to claim 1, wherein the crystalline form CSVI exhibits an X-ray powder diffraction pattern comprising one or two or three characteristic peaks at 2theta values of 11.1°±0.2°, 14.1°±0.2° and 13.1° 0.2° using CuKα radiation.

5. The crystalline form CSVI according to claim 1, wherein the crystallilne form CSVI exhibits an X-ray powder diffraction pattern is comprising as depicted in FIG. 1.

6. A process for preparing crystalline form CSVI according to claim 1, wherein the process comprises:
   1) adding upadacitinib and succinic acid into a mixture of an ester and an ether, stirring to obtain crystalline form CSVI, or
   2) adding upadacitinib and succinic acid into a mixture of an ether, an alcohol, water and an alkane, or a mixture of an alcohol and an alkane, stirring to obtain crystalline form CSVI.

7. The process according to claim 6, wherein said ester is isopropyl acetate, said ether is methyl tert-butyl ether, said alcohol is n-propanol, isopropanol, isobutyl alcohol or n-butanol, said alkane is n-heptane.

8. A crystalline form CSVII of upadacitinib, wherein crystalline form CSVII is a co-crystal of upadacitinib and adipic acid

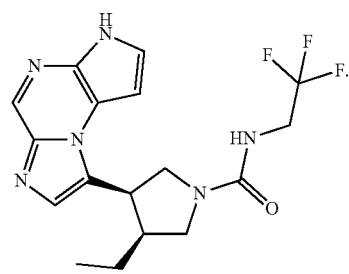 [SMILES: CC[C@@H]1CN(C(=O)NCC(F)(F)F)C[C@@H]1c1cnc2cnc3[nH]ccc3n12]

9. The crystalline form CSVII according to claim 8, wherein the crystalline form CSVII exhibis an X-ray powder diffraction pattern comprising one or two or three characteristic peaks at 2theta values of 4.8°±0.2°, 6.0°±0.2° and 22.4°±0.2° using CuKα radiation.

10. The crystalline form CSVII according to claim 8, wherein crystalline form CSVII exhibits an X-ray powder diffraction pattern comprising one or two or three characteristic peaks at 2theta values of 21.1°±0.2°, 15.4°±0.2° and 16.2°±0.2° using CuKα radiation.

11. The crystalline form CSVII according to claim 8, wherein the crystalline form CSVII exhibits an X-ray powder diffraction pattern comprising one or two or three characteristic peaks at 2theta values of 25.4°±0.2°, 12.8°±0.2° and 20.2°±0.2° using CuKα radiation.

12. The crystalline form CSVII according to claim 8, wherein the crystalline form CSVII exhibits an X-ray powder diffraction pattern as depicted in FIG. 6.

13. A process for preparing crystalline form CSVII according to claim 8, wherein the process comprises:
   1) adding upadacitinib and adipic acid into a mixture of an ester and an ether, stirring to obtain crystalline form CSVII, or
   2) adding upadacitinib and adipic acid into a mixture of an alcohol and an alkane, stirring, isolation, and then drying to obtain crystalline form CSVII.

14. The process according to claim 13, wherein said ester is isopropyl acetate, said ether is methyl tert-butyl ether, said alcohol is n-propanol, isopropanol, n-butanol or isobutyl alcohol, said alkane is n-heptane.

15. A pharmaceutical composition, wherein said pharmaceutical composition comprises a therapeutically effective amount of crystalline form CSVI according to claim 1 and pharmaceutically acceptable excipients.

16. A pharmaceutical composition, wherein said pharmaceutical composition comprises a therapeutically effective amount of crystalline form CSVII according to claim 8, and pharmaceutically acceptable excipients.

* * * * *